United States Patent
Volkau et al.

(10) Patent No.: US 8,311,359 B2
(45) Date of Patent: Nov. 13, 2012

(54) REGISTERING BRAIN IMAGES BY ALIGNING REFERENCE ELLIPSES

(75) Inventors: Ihar Volkau, Singapore (SG); Bhanu Prakash K. N., Singapore (SG); Ting Ting Ng, Singapore (SG); Varsha Gupta, Singapore (SG); Wieslaw Lucjan Nowinski, Singapore (SG)

(73) Assignee: Agency for Science, Technology and Research, Centros (SG)

( * ) Notice: Subject to any disclaimer, the term of this patent is extended or adjusted under 35 U.S.C. 154(b) by 709 days.

(21) Appl. No.: 12/306,842

(22) PCT Filed: Jun. 28, 2007

(86) PCT No.: PCT/SG2007/000188
§ 371 (c)(1),
(2), (4) Date: Sep. 25, 2009

(87) PCT Pub. No.: WO2008/002275
PCT Pub. Date: Jan. 3, 2008

(65) Prior Publication Data
US 2010/0040264 A1     Feb. 18, 2010

Related U.S. Application Data

(60) Provisional application No. 60/816,876, filed on Jun. 28, 2006.

(51) Int. Cl.
*G06K 9/40* (2006.01)

(52) U.S. Cl. ........ 382/262; 382/128; 382/154; 382/282; 382/284

(58) Field of Classification Search ................... 382/128, 382/154, 262, 282, 284
See application file for complete search history.

(56) References Cited

U.S. PATENT DOCUMENTS

| | | | |
|---|---|---|---|
| 5,926,568 A | 7/1999 | Chaney et al. | |
| 7,103,203 B2 * | 9/2006 | Deschamps | 382/128 |
| 7,181,058 B2 * | 2/2007 | Weisgerber et al. | 382/145 |
| 7,830,378 B2 * | 11/2010 | Inoue et al. | 345/424 |
| 8,045,770 B2 * | 10/2011 | Reeves et al. | 382/128 |
| 2003/0228042 A1 | 12/2003 | Sinha | |
| 2005/0027187 A1 | 2/2005 | Barth et al. | |
| 2005/0111719 A1 | 5/2005 | Pescatore et al. | |

OTHER PUBLICATIONS

International Search Report Issued in International Application PCT/SG2007/000188 dated on Apr. 2007.

* cited by examiner

*Primary Examiner* — Yosef Kassa
(74) *Attorney, Agent, or Firm* — McDermott Will & Emery LLP

(57) ABSTRACT

In a method of registering three-dimensional brain images, a reference slice for a midsagittal plane of each image is constructed. The reference slice comprises image points forming a cortical edge. Edge points are selected from these image points such that an ellipse fit to the edge points approximates the cortical edge. The reference ellipse in each image that fits the edge points is determined. The images are registered in a same coordinate system such that the reference ellipses in the images are aligned with one another.

17 Claims, 10 Drawing Sheets

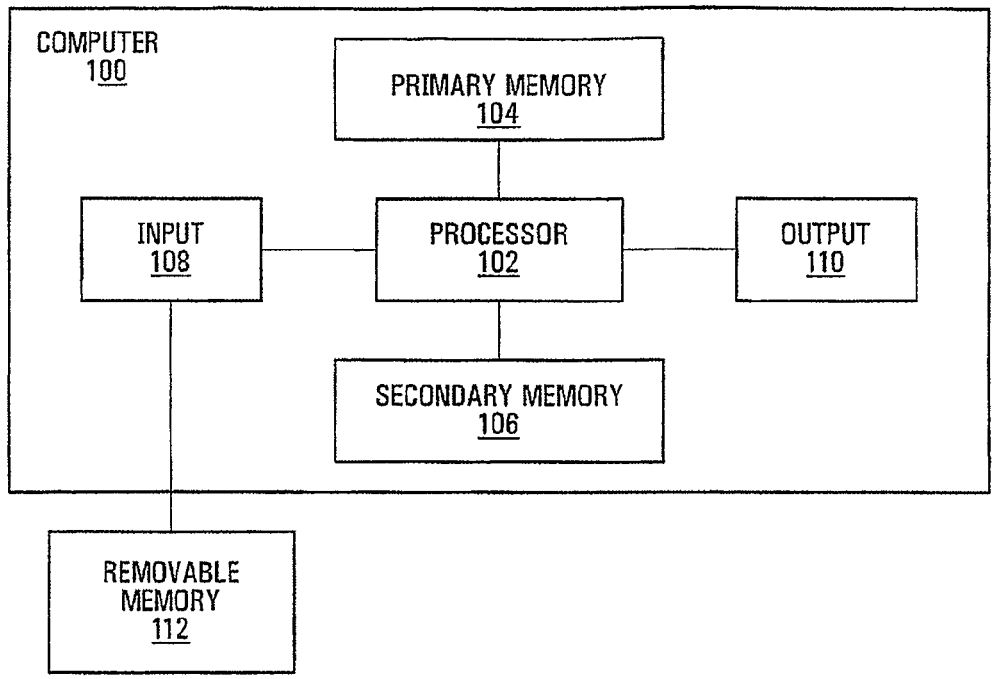
FIG. 1
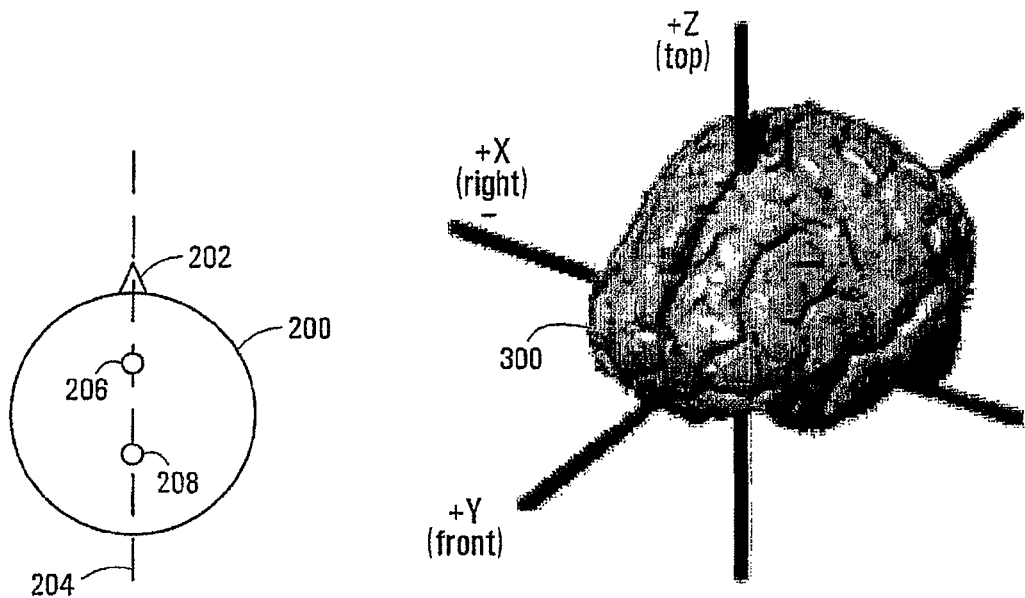
FIG. 2
FIG. 3

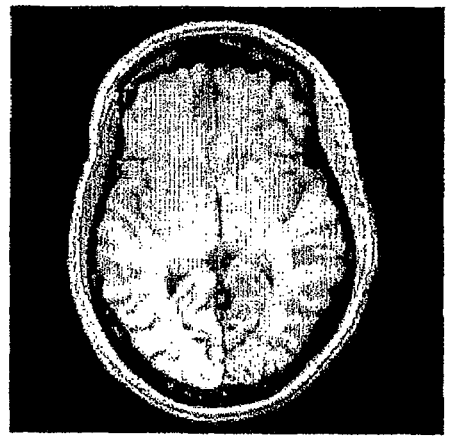
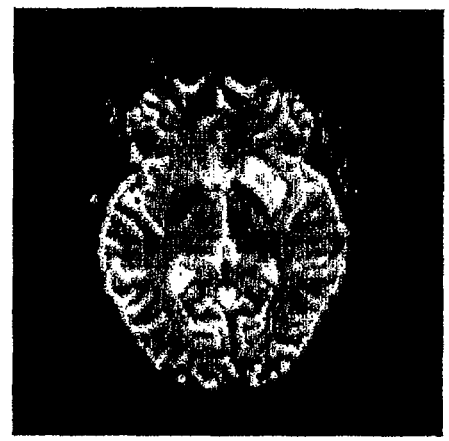
FIG. 5A  FIG. 5B
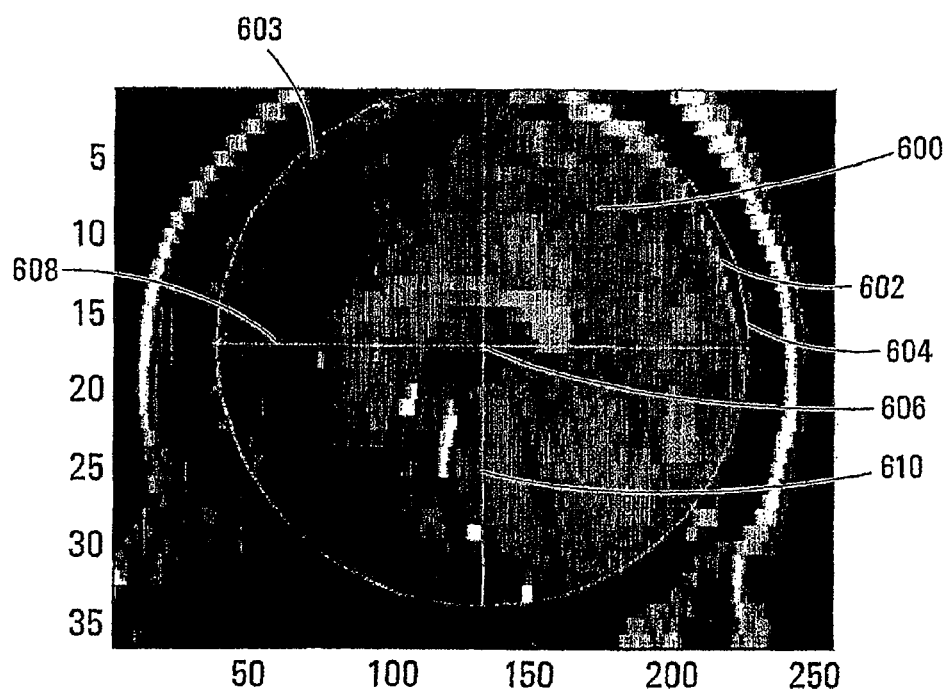
FIG. 6 ically to
method and apparatus for registering brain images of a same
patient in a same coordinate system.

REGISTERING BRAIN IMAGES BY ALIGNING REFERENCE ELLIPSES

CROSS REFERENCE TO RELATED APPLICATIONS

This application is the U.S. National Phase under 35 U.S.C. §371 of International Application No. PCT/SG2007/000188, filed on Jun. 28, 2007, which in turn claims the benefit of U.S. Provisional Application Ser. No. 60/816,876, filed Jun. 28, 2006, the contents of which are incorporated herein by reference.

FIELD OF THE INVENTION

The present invention relates generally to method and apparatus for registering brain images, and particularly to method and apparatus for registering brain images of a same patient in a same coordinate system.

BACKGROUND OF THE INVENTION

Brain image co-registration is useful in brain image processing and analysis. Neuroimage co-registration is often a prerequisite for advanced neuroimage processing and visualization. The co-registered images may be taken from the same patient (intra-patient), at different times, under different conditions, or using different imaging techniques (modalities).

There are conventional techniques for registering brain images. For example, three dimensional (3D) brain images have been registered by aligning their centroids and principal axes, or by surface fitting which minimizes the average distance between the contours extracted from two scanned images. However, these techniques provide unsatisfactory results when the scanned images are incomplete or when the directions of the principal axes in an image are inaccurately determined (e.g. because of artifacts). In another conventional technique, the images are registered by aligning imaged anatomical landmarks. However, sometimes it is difficult or impossible to detect accurately anatomical landmarks, when the images have a low resolution, or there is no manifestation of the landmarks in the image at all (e.g. when the image is a non-morphological one). Typical conventional registration techniques for three dimensional images are based on voxel analysis and require extensive computing resources.

Accordingly, it is desirable to provide an alternative registration technique that can provide relatively more accurate alignment when the registered images are of a low resolution or are incomplete. It is also desirable to provide a registration technique that requires relatively less extensive computation.

SUMMARY OF THE INVENTION

In accordance with an aspect of the present invention, there is provided a method of registering three-dimensional brain images. For each image, a reference slice for a midsagittal plane of the image is constructed. The reference slice comprises image points forming a cortical edge. The edge points are selected from the image points such that an ellipse fit to the edge points approximates the cortical edge. A reference ellipse in the image that fits the edge points is determined. The images are registered in a same coordinate system such that the reference ellipses in the images are aligned with one another. Each one of the reference ellipses has a center point, a major axis, and a minor axis. The reference ellipses may be aligned such that their center points are coincident, their minor axes are collinear and their major axes are collinear. The edge points may comprise at least 15 points. The edge points may be distributed over the cortical edge. The reference slice may be constructed from slices of the image that are parallel to the midsagittal plane and within a selected distance from the midsagittal plane. The distance may be 2 mm. The reference slice may be constructed from the slices of the image using maximum intensity projection. The images may include brain images of a same patient. The images may be of different modalities. In particular, the images may comprise perfusion and diffusion images. The alignment of the images in the coordinate system may be adjusted to match corresponding ventricle regions in the brain images. The alignment adjustment may include selecting a volume of interest (VOI) in each image; selecting an axial slice in the VOI of each image such that the selected axial slices are spatially closest to each other in the images; and determining a ventricle region in each axial slice, as one of the corresponding ventricle regions. The ventricle region may be determined by, at least in part, segmenting voxels in the axial slice into cerebrospinal fluid (CSF) voxels and non-CSF voxels; and selecting a region in the axial slice formed of CSF voxels as the ventricle region. The edge points may comprise end points determined by locating a cortical edge in an axial slice of each image; determining an axial ellipse that fits the cortical edge in the axial slice; and determining that the anterior and posterior points of the axial ellipse are the end points.

In accordance with another aspect of the present invention, there is provided a computer comprising a processor and a computer readable memory, adapted to perform the method described in the preceding paragraph.

In accordance with a further aspect of the present invention, there is provided a computer readable medium storing thereon computer executable code. The code when executed by a computer adapts the computer to perform the method described above.

Other aspects and features of the present invention will become apparent to those of ordinary skill in the art upon review of the following description of specific embodiments of the invention in conjunction with the accompanying figures.

BRIEF DESCRIPTION OF THE DRAWINGS

In the figures, which illustrate, by way of example only, embodiments of the present invention, FIG. 1 is a schematic block diagram of a computer, exemplary of an embodiment of the present invention;

FIG. 2 is a schematic top view of a human head and the midsagittal plane;

FIG. 3 shows a brain image in a coordinate system;

FIG. 5A is an axial image of a T1 brain image of a patient;

FIG. 5B is an axial image of a DWI brain image of the patient;

FIG. 6 is an image of a reference slice for a 3D brain image of the patient, determined according to the process of FIG. 4A;

DETAILED DESCRIPTION

Figure 4A:
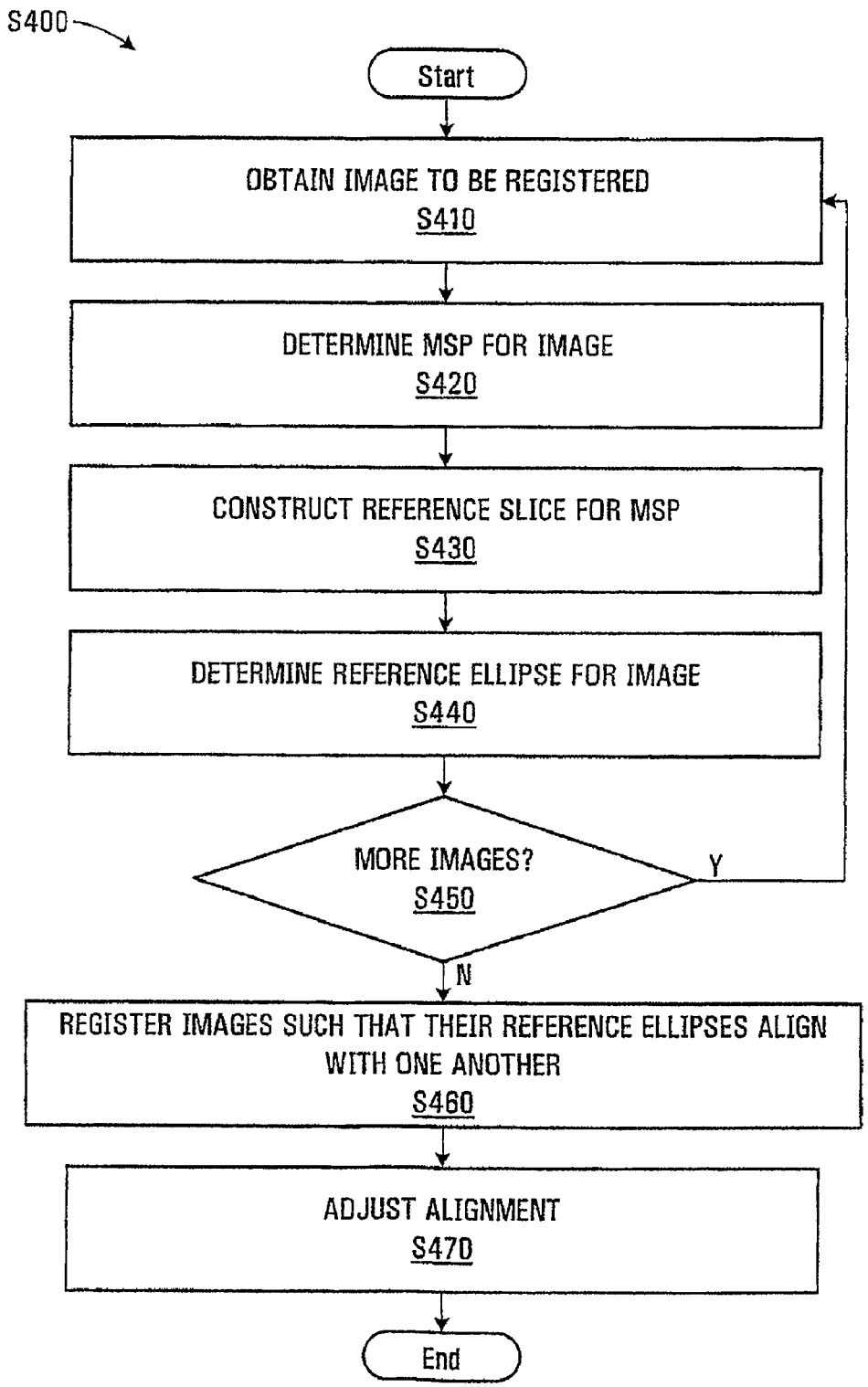
FIGS. 4A and 4B are flowcharts for a process of image registration, exemplary of an embodiment of the present invention.

In overview, in a method exemplary of embodiments of the present invention, two or more three-dimensional (3D) brain images are co-registered by aligning their respective reference ellipses. Each reference ellipse is selected so that it closely matches or approximates the cortical edge in the midsagittal plane (MSP) of the respective brain image. It has been found that registering the brain images in this manner can provide satisfactory initial alignment of the brain images for further processing and analysis. Such a method can be performed without requiring extensive computation or complete image data.

The method may be performed, at least in part, by a computer device such as computer 100 shown in FIG. 1, exemplary of embodiments of the present invention.

Computer 100 has a processor 102, which communicates with primary memory 104, secondary memory 106, input 108 and output 110. Computer 100 may optionally communicate with a network (not shown).

Processor 102 includes one or more processors for processing computer executable codes and data.

Each of memories 104 and 106 is an electronic storage comprising a computer readable medium for storing electronic data including computer executable codes. Primary memory 104 is readily accessible by processor 102 at runtime and typically includes a random access memory (RAM). Primary memory 104 only needs to store data at runtime. Secondary memory 106 may include persistent storage memory for storing data permanently, typically in the form of electronic files. Secondary memory 106 may also be used for other purposes known to persons skilled in the art. A computer readable medium may be any available media accessible by a computer, either removable or non-removable, either volatile or non-volatile, including any magnetic storage, optical storage, or solid state storage devices, or any other medium which may embody the desired data including computer executable instructions and can be accessed, either locally or remotely, by a computer or computing device. Any combination of the above is also included in the scope of computer readable medium.

Input 108 may include one or more suitable input devices, and typically includes a keyboard and a mouse. It may also include a microphone, a scanner, a camera, and the like. It may also include a computer readable medium such as removable memory 112 and the corresponding device for accessing the medium. Input 108 may be used to receive input from the user. An input device may be locally or remotely connected to processor 102, either physically or in terms of communication connection.

Output 110 may include one or more output devices, which may include a display device, such as a monitor. Suitable output devices may also include other devices such as a printer, a speaker, and the like, as well as a computer writable medium and the device for writing to the medium. Like an input device, an output device may be local or remote.

Computer 100 may communicate with other computer systems (not shown) on a network (not shown).

It will be understood by those of ordinary skill in the art that computer system 100 may also include other, either necessary or optional, components not shown in the figure.

Memory 104, 106 or 112 may be used to store image or computation data, calculation results, or other input and output data used in the registration process.

Memory 104, 106 or 112 may also store computer executable code, which when executed by processor 102 causes computer 100 to carry out any of the methods described herein. For example, the computer executable code may include code for determining MSP in a 3D brain image; code for generating a reference slice for the MSP, selecting points from a cortical edge in the reference slice, and determining a reference ellipse that fits the selected points; and code for registering multiple 3D brain images by aligning their respective reference ellipses, as will be further described below. The program code may also include code for displaying and manipulating individual 3D images, two-dimensional (2D) slices of the 3D images, the reference slices, the reference ellipses, and the co-registered images.

As can be appreciated, methods described herein may also be carried out in whole or in part using a hardware device having circuits for performing one or more of the described calculations or functions. For example, the functions of one or more of the above mentioned program code may be performed by a computing circuit.

The 3D brain images that can be registered according to embodiments of the present invention may be scanned images obtained using any suitable imaging techniques. Typical imaging techniques include magnetic resonance imaging (MRI), computerized tomography (CT), positron emission tomography PET, digital subtraction angiography (DSA), single photon emission computed tomography (SPECT), and the like. The exemplary processes described below will be illustrated with reference to a particular type of images, MRI images. Suitable MRI images include T1-weighted (T1), T2-weighted (T2), diffusion-weighted (DWI), perfusion-weighted (FWD, fast fluid-attenuated inversion-recovery (FLAIR), cerebral blood volume (CBV), and echo-planar (EPI) images, apparent diffusion coefficient (ADC) and mean-transit-time (MTT) maps, and the like. However, it is understood that embodiments of the present invention can be applied for registering other combinations of MRI or other types of images.

The images may be represented digitally using intensity histograms or maps where each voxel has a corresponding coordinate and intensity value. Image registration is a process of transforming different sets of data for different images into one coordinate system. The different images may be taken from a single patient at different times, under different conditions, or using different imaging techniques (modalities). It is desirable that the registered images are aligned properly so that the volumes of different images that represent the same region in the brain coincide in space in the coordinate system.

A typical coordinate system for brain images is the Talairach coordinate system, where the anterior commissure and posterior commissure of the brain lie in a straight horizontal line and the MSP is vertical. Typically, in a Talairach coordinate system the anterior commissure is the origin.

The location of MSP and the anterior commissure and posterior commissure in a brain is illustrated in FIG. 2, which is a schematic top view of a human head 200. As depicted, the nose 202 (the anterior end) of head 200 points upward. The MSP 204 is the medial plane that divides head 200 into left and right halves (hemispheres) and passes through the anterior commissure 206 and posterior commissure 208.

An exemplary Talairach coordinate is illustrated in FIG. 3, where the X and Y axes are horizontal and the Z axis is vertical. As depicted, a brain image 300 is registered such that the plane defined by the Y and Z axes coincides with the MSP of the brain. In this case, the anterior commissure (not shown) and posterior commissure (not shown) are on the Y-axis.

3D brain images can be registered according to the registration process S400 illustrated in FIG. 4, exemplary of embodiments of the present invention.

For the purposes of illustration and describing process S400, it is assumed that two or more 3D brain images of different modalities for the same patient are to be registered. For example, a DWI image and a PWI image of the same patient may be co-registered according to process S400. It should be understood that process S400 may be used to register more than two images of the same or different modalities, and for registration of morphological and non-morphological images.

At S410, the image data for the next image to be processed is obtained. As can be appreciated, the image data may be provided in an electronic file and may be stored on a computer readable medium, such as on secondary memory 106 or removable memory 112 (shown in FIG. 1). The image data may also be obtained from an image database stored either locally or remotely. The image data may be provided using any suitable data format. Typically, a 3D image can be represented with, or can be divided into, a number of parallel slices. A scanned 3D image is also typically obtained by obtaining scanned images of parallel planes (slices) in the imaged subject.

FIGS. 5A and 5B show exemplary axial images of two 3D brain images of a patient which are to be co-registered, where the image in FIG. 5A is a T1 image and the image in FIG. 5B is a DWI image.

The 3D images may be initially represented in the same coordinate systems or in different coordinate systems. If they are initially represented in different coordinate systems, they may be transformed into the same coordinate system before further processing. It may be more convenient for the later processing when the images are represented in the same coordinate systems.

At S420, the image data for the current image is processed to determine the MSP in the image. Any suitable techniques for determining the MSP in a brain image may be used. For example, the MSP may be located using conventional techniques including the technique described in PCT patent application publication WO 2005/096227 to KN et. al., entitled "Locating a mid-sagittal plane" and published on Oct. 13, 2005, the contents of which are incorporated herein by reference. The MSP may be described as a plane in a 3D Cartesian coordinate in the form $Ax+By+Cz+D=0$.

At S430, a reference slice is constructed for the MSP. In one embodiment, the reference slice is constructed using maximum intensity projections (MIP) of the scanned slices of the image that are within a distance of several mm, such as 2 mm, from the MSP. Such a reference slice is referred to as the MIP-MSP. Briefly, a number of the image slices that are parallel to the MSP and within a given distance from the MSP are selected. The given distance may vary depending on the extent of inter-hemispheric fissure which can be different for different specimens. The pixel intensities of the slices are projected on to the MSP such that the intensity of each pixel in the MIP-MSP equals the maximum intensity in the corresponding pixels of the selected slices. The construction of the MIP-MSP may be performed using a conventional technique such as those disclosed in Wallis J. W. et al., "Three-dimensional display in nuclear medicine", IEEE Trans. Med. Imag., 1989; vol, 8, pp. 297-303; and online at <http://en.wikipedia.org/wiki/Maximum_intensity_projection>, the contents of each of which are incorporated herein by reference.

An exemplary reference slice 600 constructed from a T1 3D brain image is illustrated in FIG. 6. As illustrated, reference slice 600 has a cortical edge 602 that represents the outline of the cortex of the imaged brain in the MSP. While the outline of the brain cortex generally does not have a perfect geometric shape, cortical edge 602 in the reference slice can be approximated by an ellipse. For different images of the same patient, it may be assumed that the ellipses derived from the different images should have approximately the same major and minor axes. Thus, by aligning the ellipses that approximate (or fit) the respective cortical edges, the imaged cortices in the different images can be properly aligned.

Therefore, at S440, a reference ellipse is determined from each reference slice.

In one embodiment, the reference slice is first processed to determine the cortical edge. The cortical edge can be marked manually or using any suitable algorithm which can correctly extract the cortex. For example, conventional software packages or tools such as the Brain Extraction Tool (BET)™ or Brain Surface Extractor (BSE)™ in the BrainSuite™ software package, may be used to determine the cortical edge. Further details of BET may be found online at <http://citeseer.ist.psu.edu/492470.html> and further details of BSE and BrainSuite may be found online at <http://brainsuite.usc.edu/>, the contents of each of which are incorporated herein by reference.

The reference ellipse is determined so that it approximates or fits the cortical edge of the brain in the reference slice.

For example, a general elliptical equation, such as in the form of $Ay^2+Byz+Cz^2+Dy+Ez+F=0$ (assuming the MSP is in the Y-Z plane), may be used to fit the data points on the cortical edge. The ellipse can also be represented by its parameters: coordinate of the centerpoint, major and minor axes and inclination. To avoid inaccuracies caused by inaccurate automatic brain extraction, edge points on the cortical edge may be selected manually. The fitting may be performed using the selected edge points 603 (shown as crosses in FIG. 6A) on cortical edge 602. Theoretically, the minimum number of edge points 603 required for each image is 5, as an ellipse has five degrees of freedom. A smaller number of edge points may require less computation to fit. However, the number of selected edge points should be sufficiently large and the selected edge points should be sufficiently distributed such that an ellipse fit to the selected edge points approximates the cortical edge. In practice, it has been found that to determine an adequate reference ellipse, the number of selected edge points 603 for each image should be at least 15. The edge points may be located between pre-selected frontal and occipital points on the cortex edge. It may be advantageous if the edge points are distributed over the entire cortical edge and enclose the entire cortex region including the frontal and occipital cortices. In some embodiments, it may be advantageous if the edge points are generally evenly distributed but are denser in sections of the cortical edge that have a large curvature. In some embodiments, all points on the cortical edge may be selected as edge points when there is sufficient computation resource.

In some cases, additional measures may need to be taken to ensure the cortical edge is accurately determined. For example, in a DWI image, the susceptibility artifacts can cause the cortical edge in the MSP to either expand or shrink. To correct for this artifact effect, the following procedure may be taken. Axial slices of the scanned image are analyzed to locate a cortical edge in each of these axial slices. As is conventional, axial slices in a brain image refer to slices that are parallel to the axial (or transverse) plane of the brain (in FIG. 2 the axial plane is parallel to the X-Y plane). For a given axial slice, the axial ellipse that fits the cortical edge in the axial slice is determined, such as in a manner similar to the determination of the reference ellipse described above. The anterior and posterior points of the ellipses in these axial slices are determined and used as the (anterior and posterior) end points of the cortical edge in the reference slice for determining the reference ellipse for the MSP. That is, the cortex edge points include these end points. In this manner, the artifacts effect can be reduced.

Points on the cortical edge in the reference slice are selected between the orbito-frontal and infero-occipital point landmarks. These landmarks may be selected manually. The points on the cortical edge of the brain can be selected manually or using a suitable automated method which provides the contour of the cortex. An automated method may include a segmentation algorithm for segmenting the cortex regions from other regions, as can be understood by persons skilled in the art.

In one embodiment, when the cortical edge is determined automatically, all points on the cortex edge between the given landmarks may be used to determine the reference ellipse. In another embodiment, when the edge points are chosen manually, at least 15 edge points should be manually selected for fitting the reference ellipse.

The selected edge points on the cortical edge are fit to an elliptical equation to determine the corresponding reference ellipse. The fitting of ellipses to the data points may be performed using any suitable technique. Conventional techniques for fitting ellipses to data points may be used, including the technique described in Fitzgibbon A. et al., "Direct Least Square Fitting of Ellipses," IEEE Transactions on Pattern Analysis and Machine Intelligence, May 1999, vol. 21, pp. 476-480, the contents of which are incorporated herein by reference.

The reference ellipse 604 for reference slice 600 is also illustrated in FIG. 6. As depicted, ellipse 604 has a center point 606, a major axis 608 and a minor axis 610. As the axes of the ellipse may not be aligned with the coordinate axes in the MSP (such as the Y-axis in FIG. 3), axes 608, 610 may be inclined at an angle with reference to the coordinate axes (such as the Y-axis). An ellipse is fully defined in a given coordinate system by its center point, major and minor axes and the inclination angle of the axes with reference to a given coordinate axis. In one embodiment, the inclination angle may be calculated with respect to the Y-axis, referred to as the angle with abscissa.

At S450, if there is any further image to be registered the next image is processed by returning to S410 and repeating the above described process.

If the reference ellipses for all images have been determined, the images are registered to the same coordinate system by requiring that the reference ellipses align with each other (at S460). Two ellipses are aligned when their center points are coincident, their minor axes are collinear and their major axes are collinear.

The alignment of the ellipses may be carried out by first aligning the center points through translation of one ellipse, and then aligning the axes through rotation of one or both ellipses around the common center point. As can be appreciated, when two ellipses are of the same size, their alignment may also be carried out by aligning the points on the ellipses directly or by aligning their foci. The other image points in the respective image are transformed with the respective ellipse so that their relative spatial relationship with the corresponding ellipse preserved (referred to as rigid registration). The two images so registered in the same coordinate system have a good initial alignment, which may further fine tuned as described below.

In an ideal situation, the ellipses derived from different images are of the same shape and size (or of the same ellipse parameters), as they are fit to the same cortical outline in the MSP of the same patient. In practice, this may not be the case. The MSP determined from different images of different modalities may be different due to the fact that the determination of MSP can be affected by certain properties of the image which manifest differently in images of different modalities, such as MRI with different pulse sequences. To obtain more accurate results, such effects should be taken into account and measures be taken to correct the possible distortions during the MSP finding and ellipse fitting.

It has been discovered that it can be expected that the center of the reference ellipse lies at the cross-section of the MSP and the interthalamic adhesion (massa intermedia). In the brain images of most patients, the interthalamic adhesion is visible. In some human brains, however, the interthalamic adhesion may be missing.

To correct for the mis-alignment of the MSP in different images, the alignment of the images in the coordinate system may be adjusted at S470.

In one embodiment, for each 3D image, an axial slice at a selected distance, such as 25 mm, above (i.e. in the inferior-superior direction) the center of the reference ellipse may be used to adjust the alignment. The axial slices are first processed to determine the ventricle regions therein, and then aligned to match the corresponding ventricle regions, through translation and rotation (rigid registration).

Figure 4B:
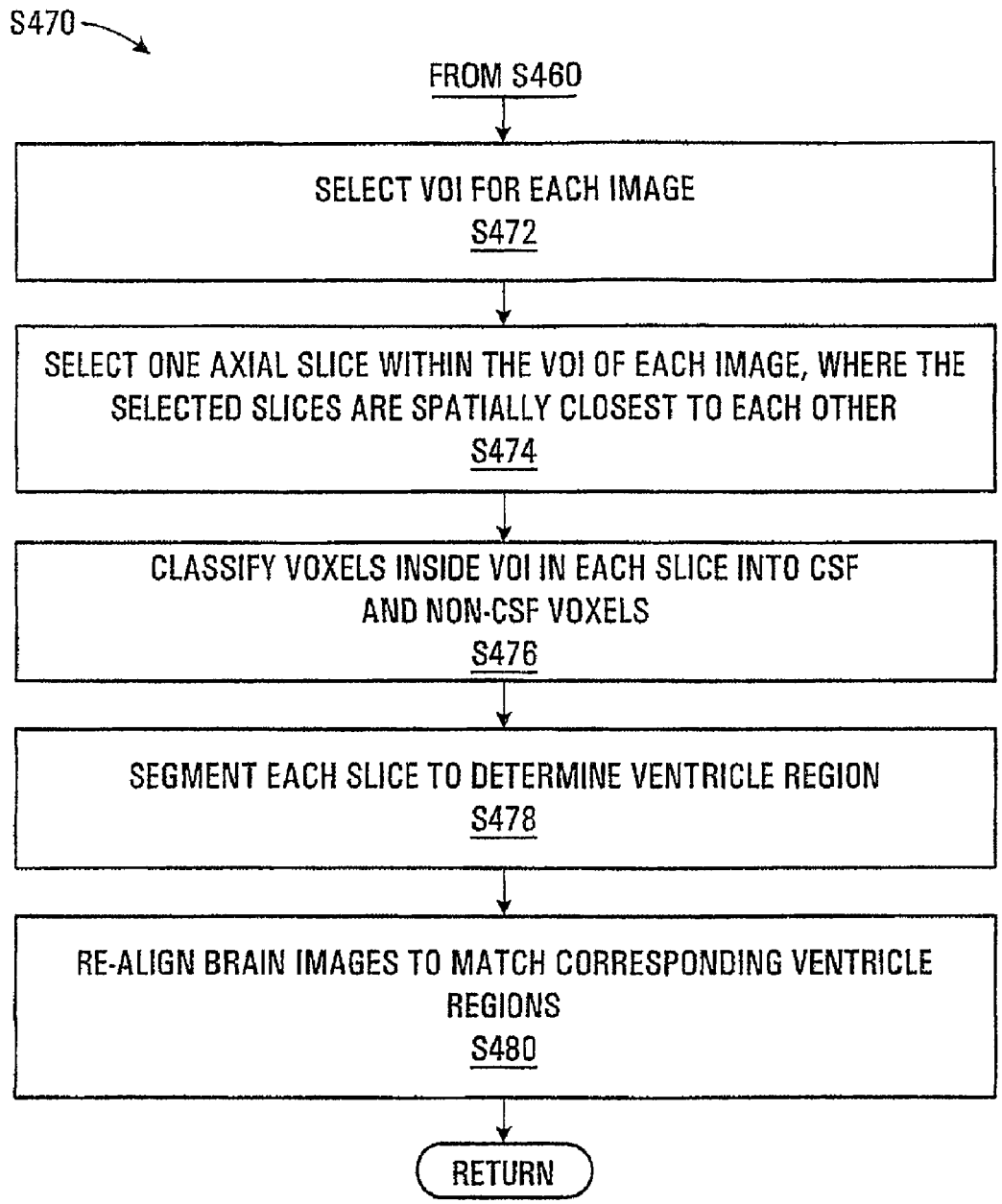

This process is illustrated in more detail below using DWI images and mean transit time (MTT) map of PWI images, and the exemplary fine tuning process S470 shown in FIG. 4B. The algorithm may be adapted to align two images at a time. In case where three or more images are to be aligned, two of the images may be aligned first and the subsequent images may be subsequently aligned to one of the two aligned images. All of the images may be aligned with reference to a selected reference image.

At S472, a volume of interest (V01) for each registered image is determined. For example, the VOI may be a 50×50× 25 mm parallelepiped volume, where the center of its lower facet is coincident with the center of the corresponding reference ellipse. In one embodiment, the VOI is common to all registered images.

At S474, one axial slice within the VOI of each image is chosen such that the chosen slices from different images are spatially closest to each other when the images are co-registered by aligning the reference ellipses. As the axial slices in different images may have different interslice gaps, and the slices in one image may not be parallel to the slices in another image after co-registration using the reference slice, the distance between two slices from two different images (referred to as inter-image slices) may vary. Within the VOI, each pair of inter-image slices has a minimum distance, which is referred to as the distance between the pair of slices. One can find a particular pair of inter-image slices within the VOI that has the smallest distance between the pair. This particular pair of inter-image slices are referred to as spatially closest to each other within the VOI. In one embodiment, the axial slices may be selected manually by a user. In another embodiment, the axial slices may be selected using a computer with a distance finding algorithm, as can be understood by persons skilled in the art.

At S476, the voxels within the VOI in each selected slice are classified into two classes, cerebrospinal fluid (CSF) voxels and non-CSF voxels, using a segmentation algorithm, such as the algorithm described in Otsu N., "A Threshold Selection Method from Gray-Level Histogram," *IEEE Trans. Systems, Man, and Cybernetics,* 1979, vol. 9, pp. 62-66, the contents of which are incorporated herein by reference.

At S478, for each brain image, the axial slice selected at S474 is segmented based on the voxel classification at S476. That is, the selected axial slice is segmented into CSF voxels and non-CSF voxels. In each segmented axial slice, a region formed by CSF voxels is selected as one of the ventricle regions to be matched. The ventricle regions are selected so that they correspond to each other in the different images.

Figure 7A:
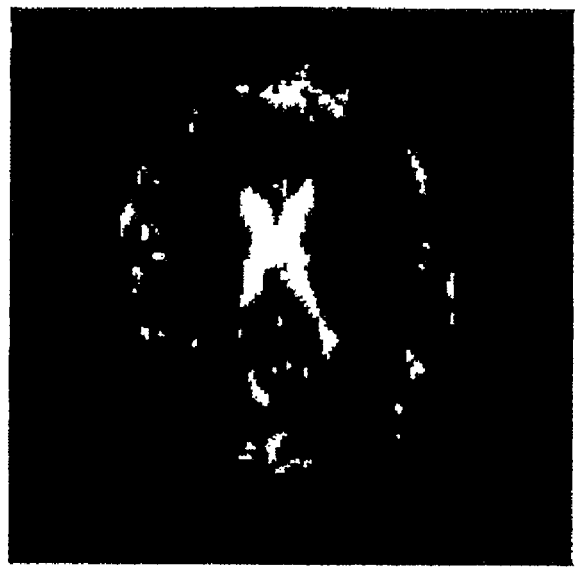
FIG. 7A is an image of an axial slice of a MTT brain image of another patient after ventricle extraction and CSF segmentation.

FIG. 7A shows an axial slice of a MTT map selected and segmented according to the procedure described above (from S472 to S478). The bright regions in the center of the image (inside the VOI) are the results of segmentation of ventricle regions.

Figure 7B:
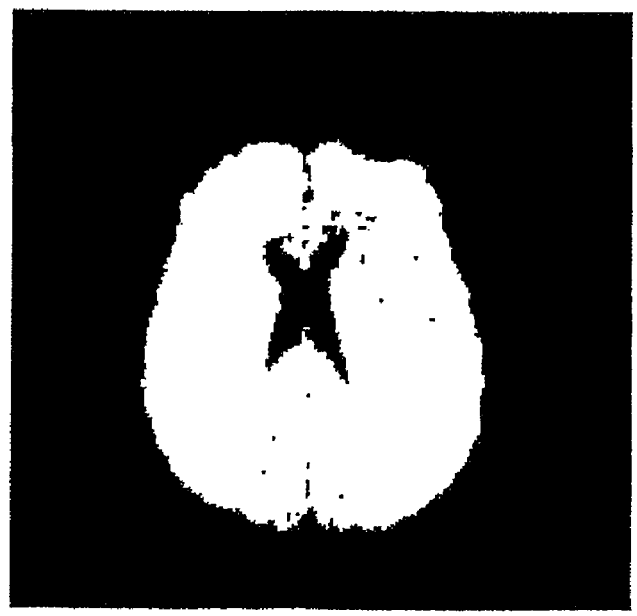
FIG. 7B is an image of an axial slice of a DWI brain image of the patient after ventricle extraction and CSF segmentation.

FIG. 7B shows an axial slice of a DWI image selected and segmented according to the procedure described above (from S472 to S478). The dark regions in the center of the image (inside the VOI) are the results of segmentation of ventricle regions.

At S480, the DWI and MTT images are re-aligned by translation and rotation (rigid registration) to match the corresponding ventricle regions in the selected axial slices.

In cases where the interslice gaps are large, the images may be translated and rotated within the axial plane only. In cases where the interslice gaps are small, the images may be translated and rotated in any of the axial, sagittal and coronal planes. For different scans, the interslice gaps may not be the same. In fast scans, a PWI/DWI image may have an interslice gap from 5 to 7 mm. The interslice gap may be considered large when it is larger than 5 mm. When the spatial resolution of the scanned image is poor and the interslice gap is relatively large, imaging information about the tissues inside the interslice gaps is lacking so that it may not be possible to accurately interpolate the voxels in the interslice gaps. As the scanned slices are typically axial slices, it may not be possible to properly translate and rotate the images in the sagittal or coronal planes during registration. However, if the interslice gap is small, translation and rotation in all three planes may be possible.

Figure 7C:
FIG. 7C is a superposition of the images of FIGS. 7A and 7B, with their ventricles aligned.

FIG. 7C shows the axial slices of FIGS. 7A and 7B superposed together and aligned to match the corresponding ventricle regions. The images may be realigned to obtain the maximum overlap of the ventricle regions. The results of the alignment may be visually verified by a user.

As alluded to earlier, computer 100 may be adapted to perform process S400. For example, computer program codes may be stored in memory 104, 106, or 112, which when executed by processor 102, adapts computer 100 to perform the process. The computer program may include available medical imaging processing tools. For example, the known software package Matlab™ may be adapted to perform this method. Additionally, as discussed above, the skull stripping tools (BSE) from BrainSuite may be used to extract the cortical edge.

As now can be appreciated, the methods and devices described herein may be useful in many different applications. For example, the exemplary registration method and device described above may be used to register low resolution DWI and PWI images, such as to find DWI-PWI mismatch to detect different patterns of abnormalities. The registration process may be performed using less computing resource than is required by some conventional registration techniques. The exemplary embodiments may provide a good initial alignment even when the images do not contain complete information, such as in the image of FIG. 8 where the superior portion of the brain is missing. Embodiments of the present invention may be used in neuroimage processing and visualization, or for stroke analysis. They can also be used in other imaging applications such as brain tumor study, diagnosis, and treatment, and the like.

The exemplary method allows alignment of morphological images, or non-morphological images, or a combination of morphological and non-morphological images, when there are no distinguishable anatomical structures in the non-morphological images but the cortical surface is visible. It also allows alignment of images of different modalities. It can be used to align low quality, low in-plane resolution, and large voxel-volume scans.

EXAMPLES

In the examples, the images shown in FIGS. 8A to 8F are from the same patient

Example I

In Example I, four different MRI images of the patient were taken, which included a T1 image, a T2 image, a FLAIR image and a DWI image. The images were manually co-registered and made to have the same dimensions and voxel sizes. Each image had a dimension of 256×256×36 (in unit of voxels in the X, Y and Z directions respectively). The voxel size was 0.898 mm×0.898 mm×3.9 mm (X-Y-Z).

The parameters of the reference ellipses were determined according to the following process:

The MSP was determined according to S420 in process S400. The MIP-MSP was determined according to S430. At least 15 edge points were manually selected according to S440, and the reference ellipse parameters were determined by fitting an ellipse to the selected points. The results are listed Table I. The coordinates and lengths in the tables are expressed in voxels.

TABLE I

Parameters of Ellipses in Example I

| Modality | Center | | Axes | | Angle with abscissa |
| | X | Y | Major | Minor | In degrees |
| --- | --- | --- | --- | --- | --- |
| T1 | 131.3933 | 16.93318 | 95.53503 | 17.02006 | 0.03889818 |
| T2 | 131.1923 | 17.06116 | 94.63400 | 16.38687 | 0.21043591 |
| FLAIR | 133.5794 | 16.93385 | 94.01440 | 16.31871 | 0.46287394 |
| DWI | 131.2385 | 17.06543 | 95.92048 | 16.48779 | 0.19283157 |

Figure 8A:
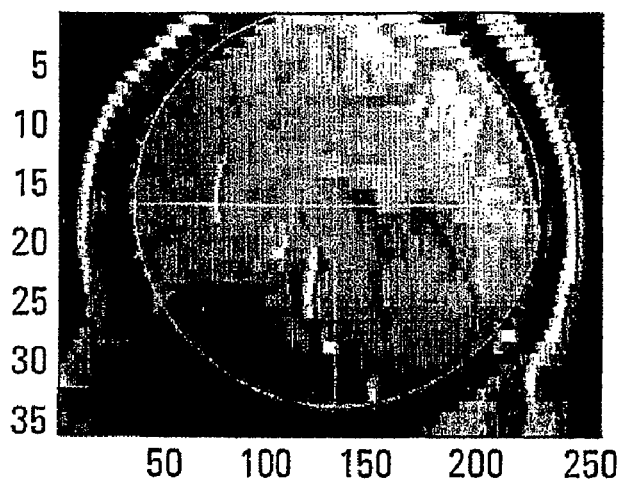
FIG. 8A is an image of a reference slice for the T1 brain image of the patient.
Figure 8B:
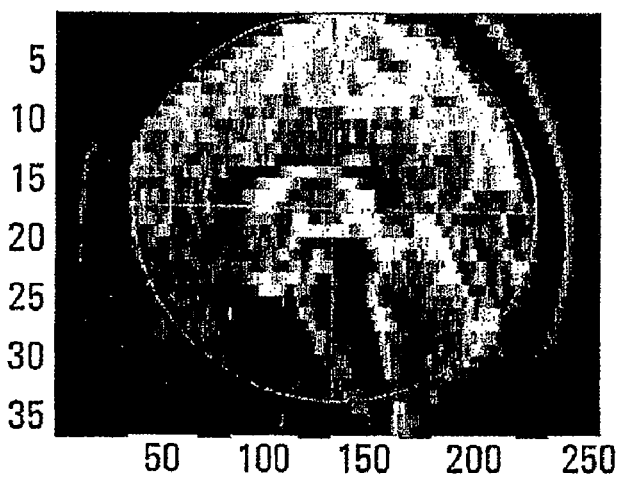
FIG. 8B is an image of a reference slice for a T2 brain image of the patient.
Figure 8C:
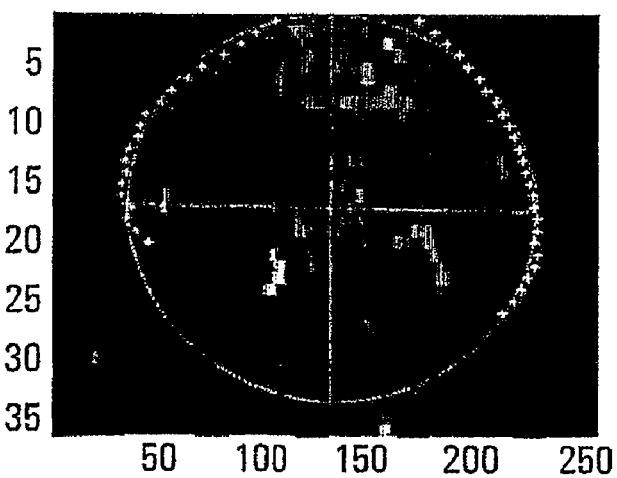
FIG. 8C is an image of a reference slice for the DWI brain image of the patient.

FIGS. 8A, 8B and 8C show the reference slices constructed according the process described above, with the corresponding reference ellipses marked thereon, for the T1, T2, and DWI images respectively.

Figure 8D:
FIG. 8D is an axial view of superposed brain images of FIGS. 8A and 8C with their reference ellipses aligned.
Figure 8E:
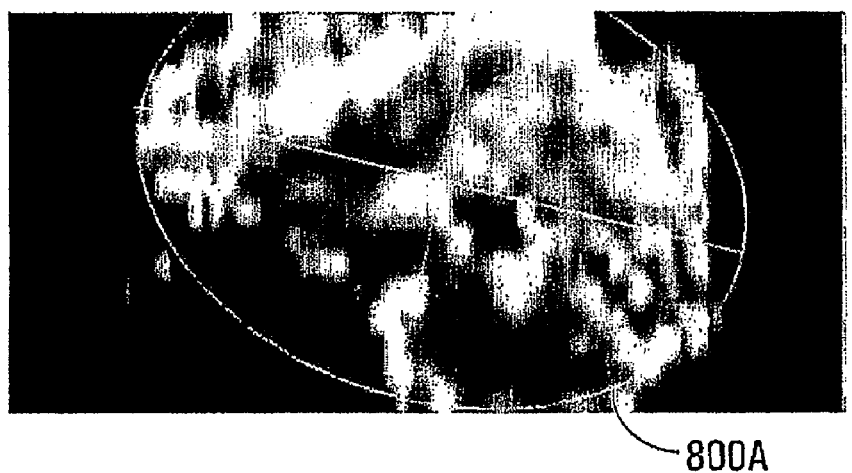
FIG. 8E is an image of a reference slice for a CBV brain image of the patient.
Figure 8F:
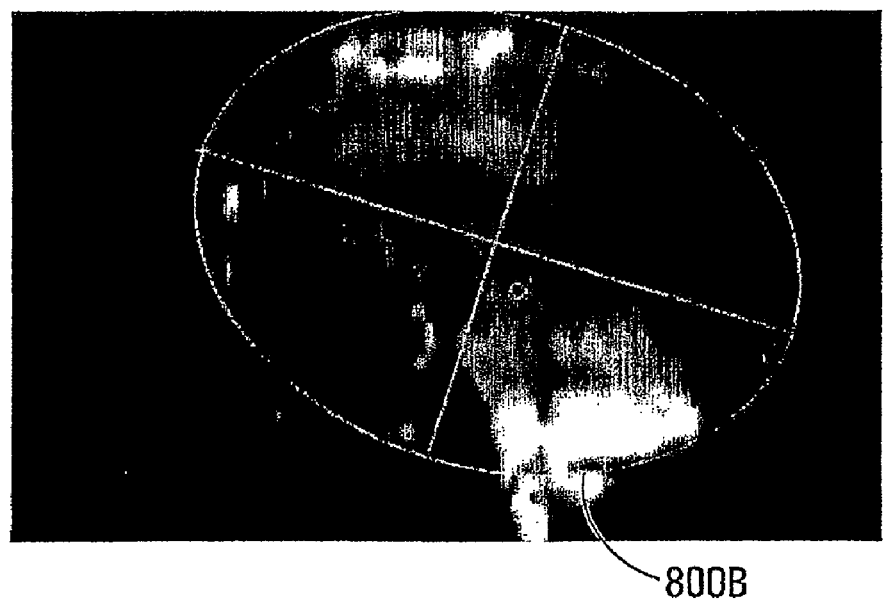
FIG. 8F is an image of a reference slice for a DWI brain image of the patient.

FIG. 8D shows an axial image of the co-registered T1 and DWI images, which were registered so that their reference ellipses were aligned.

Example II

In this example, four different MRI images of the same patient were taken, which included a T1 image, 2 DWI images, and a DWI-EPI ADC image. The images were manually co-registered and made to have the same dimensions and voxel sizes. Each image had a dimension of 256×256×37 (in voxels, in the X-Y-Z directions respectively). The voxel size was 0.898 mm×0.898 mm×3.9 mm (X-Y-Z).

The parameters of the reference ellipses for these images were determined according to the same process as in Example I, which are listed Table II.

TABLE II

Parameters of Ellipses in Example II

| Modality | Center | | Axes | | Angle with abscissa |
| | X | Y | Major | Minor | In degrees |
| --- | --- | --- | --- | --- | --- |
| T1 | 135.7340 | 18.96275 | 88.64583 | 16.69904 | 0.727569 |
| DWI-ALT-b | 135.0449 | 18.90004 | 86.07923 | 16.57087 | 0.349764 |
| DWI-ALT-2-b | 136.0979 | 18.68635 | 85.70025 | 16.28368 | 0.103201 |
| DWI-EPI_ADC | 135.0731 | 19.00680 | 87.37678 | 16.75864 | 0.348703 |

The image datasets used in Examples I and II had been previously co-registered using different methods. The registration results were thus verified against the previous results. As can be seen from Tables I and II, the coordinates of the ellipse center and the angles with abscissa were similar in each table, indicating that the errors of registration were relatively small.

Example III

Figure 8G:
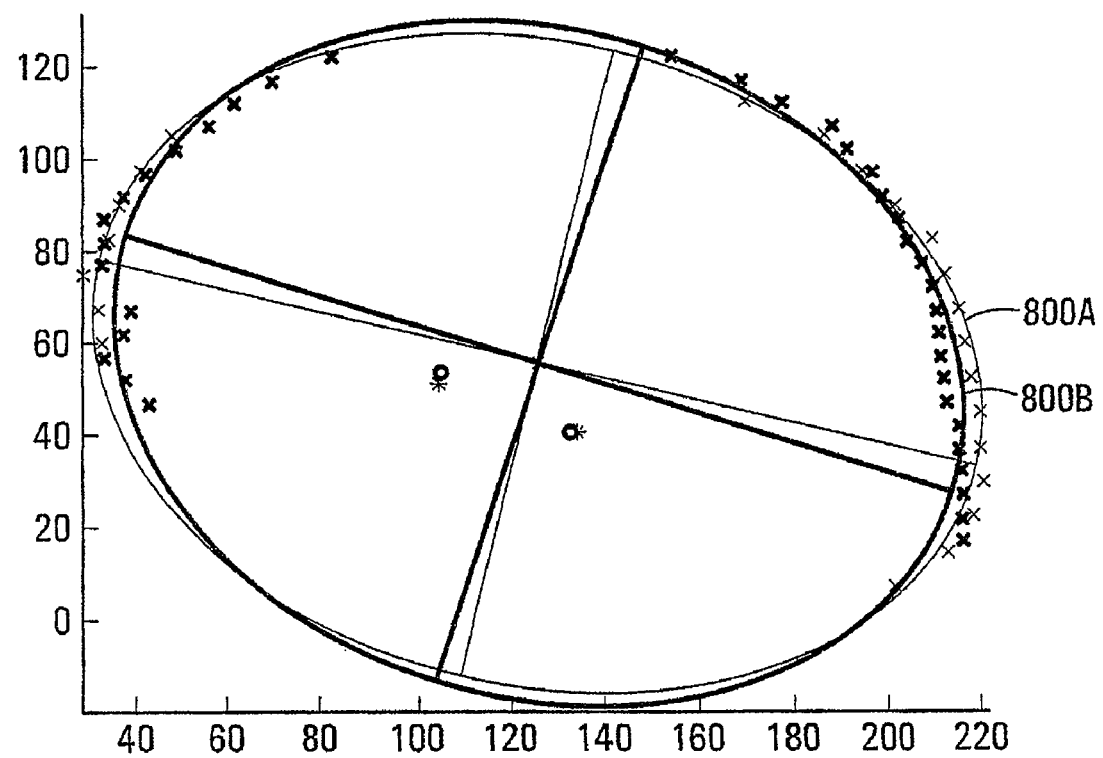
FIG. 8G shows the reference ellipses shown in FIGS. 8E and 8F with their center points aligned.

In this example, two stroke images were processed to find the respective reference ellipses, according to the same process as in Example I but with the exception that the end points of the cortical edges were determined using axial slices to minimize the artifact effects, as described earlier. The CBV image had a dimension of 256×256×15 and the voxel size was 1.0 mm×1.0 mm×7.5 mm. The DWI image had a dimension of 256×250×31 and the voxel size was 1.0 mm×1.0 mm×5.0 mm. The reference slices for the two images and the determined ellipses 800A, 800B are respectively shown in FIGS. 8E and 8F. The image shown in FIG. 8E was a CBV image and the image shown in FIG. 8F was a DWI image. Ellipses 800A, 800B are also shown in FIG. 8G, where the center points were aligned with each other by translation of ellipse 800B. As shown in FIG. 8G, the axes of ellipses 800A, 800B were not aligned. It is expected that the difference in the direction of the two sets of axes reflects the difference in head inclination during imaging. The PWI and DWI images in this example can be aligned in the same manner as shown at FIGS. 7A and 7B. MTT and CBV images are perfusion maps.

Other features, benefits and advantages of the embodiments described herein not expressly mentioned above can be understood from this description and the drawings by those skilled in the art.

The contents of each reference cited above are hereby incorporated herein by reference.

Of course, the above described embodiments are intended to be illustrative only and in no way limiting. The described embodiments are susceptible to many modifications of form, arrangement of parts, details and order of operation. The invention, rather, is intended to encompass all such modification within its scope, as defined by the claims.

What is claimed is:

1. A method of registering three-dimensional brain images, comprising:
for each one of said images,
constructing a reference slice for a midsagittal plane of said each image, said reference slice comprising image points forming a cortical edge;
selecting edge points from said image points such that an ellipse fit to said edge points approximates said cortical edge;
determining a reference ellipse in said each image that fits said edge points; and
registering said images in a same coordinate system such that the reference ellipses in said images are aligned with one another.

2. The method of claim 1, wherein each one of said reference ellipses has a center point, a major axis, and a minor axis; and wherein said reference ellipses are aligned such that their center points are coincident, their minor axes are collinear and their major axes are collinear.

3. The method of claim 1, wherein said edge points are distributed over said cortical edge.

4. The method of claim 1, wherein said reference slice is constructed from slices of said each image that are parallel to said midsagittal plane and within a selected distance from said midsagittal plane.

5. The method of claim 4, wherein said distance is 2 mm.

6. The method of claim 4, wherein said reference slice is constructed from said slices of said each image using maximum intensity projection.

7. The method of claim 1, wherein said images comprise brain images of a same patient.

8. The method of claim 1, wherein said images are of different modalities.

9. The method of claim 8, wherein said images comprise diffusion images.

10. The method of claim 8, wherein said images comprise perfusion images.

11. The method of any one of claim 1, comprising adjusting alignment of said images in said coordinate system to match corresponding ventricle regions in said brain images.

12. The method of claim 11, comprising:
selecting a volume of interest (VOI) in each one of said images;
selecting an axial slice in said VOI of said each image such that the selected axial slices are spatially closest to each other within said VOI of said images; and
determining a ventricle region in each one of said axial slices, as one of said corresponding ventricle regions.

13. The method of claim 12, wherein said determining said ventricle region comprises:
segmenting voxels in said each axial slice into cerebrospinal fluid (CSF) voxels and non-CSF voxels; and
selecting a region in said each axial slice formed of CSF voxels as said ventricle region.

14. The method of claim 1, wherein said edge points comprise end points determined by:
locating a cortical edge in an axial slice of said each image;
determining an axial ellipse that fits said cortical edge in said axial slice; and
determining that the anterior and posterior points of said axial ellipse are said end points.

15. The method of claim 1, wherein said edge points comprise at least 15 points.

16. A computer comprising a processor and a computer readable memory, adapted to perform the method of claim 1.

17. A computer readable medium storing thereon computer executable code, said code when executed by a computer adapts said computer to perform the method of claim 1.

* * * * *